United States Patent [19]

Haynes

[11] Patent Number: 4,624,129

[45] Date of Patent: Nov. 25, 1986

[54] ACOUSTICAL DRY PRODUCT DENSITY SENSOR

[76] Inventor: Joel E. Haynes, 18316 Oxnard St., Tarzana, Calif. 91356

[21] Appl. No.: 723,476

[22] Filed: Apr. 15, 1985

[51] Int. Cl.⁴ .............................................. G01N 9/00
[52] U.S. Cl. .................................................... 73/32 A
[58] Field of Search ..................... 73/32 A, 32 R, 579; 141/83

[56] References Cited

U.S. PATENT DOCUMENTS

| | | | |
|---|---|---|---|
| 3,925,850 | 12/1975 | Lytton | 73/32 A |
| 3,999,421 | 12/1976 | Creswick | 73/32 A |
| 4,182,383 | 1/1980 | Adomitis et al. | 141/83 |
| 4,407,108 | 10/1983 | Craig | 141/83 |
| 4,507,582 | 3/1985 | Glenn | 73/644 |
| 4,522,068 | 6/1985 | Smith | 73/32 A |

FOREIGN PATENT DOCUMENTS 0032846  2/1984  Japan .................... 73/32 A

Primary Examiner—Stewart J. Levy
Assistant Examiner—Robert R. Raevis
Attorney, Agent, or Firm—Charmasson & Holz

[57] ABSTRACT

A device for installation on the auger filler cone of dry product dispensing equipment which comprises one or more ultrasonic resonators arranged so as to measure the acoustic impedance of the product within the auger filler cone without interfering with the flow of the augered product. The acoustic impedance can be calibrated to give a density measurement. The device is particularly well-suited for measuring the density of a dry product in the dispensing equipment used in the packaging industry, where a specified amount by weight must be dispensed into containers. Since an auger-type filling machine dispenses a precise volume for each degree of rotational movement of the auger, constant monitoring of the density of the product within the auger cone allows the weight of the dispensed product to be rapidly and accurately determined during the filling process.

8 Claims, 8 Drawing Figures

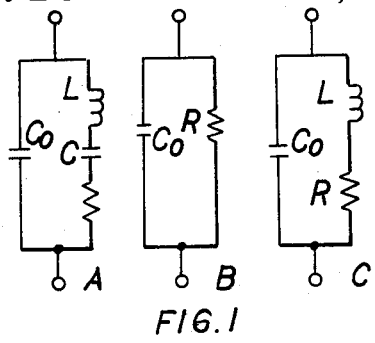
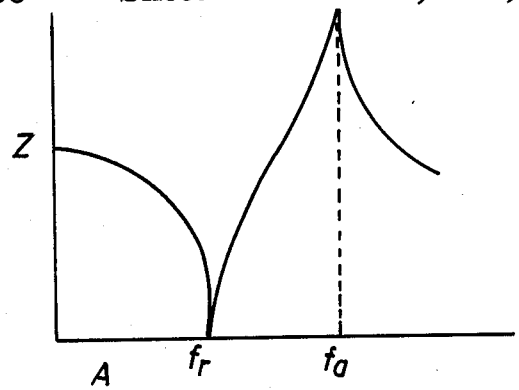
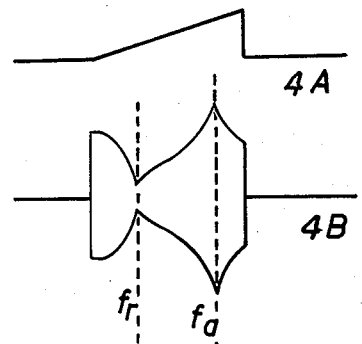
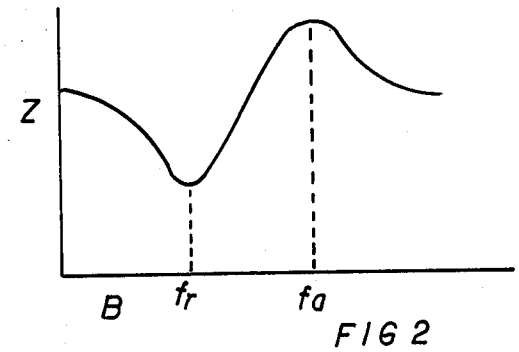
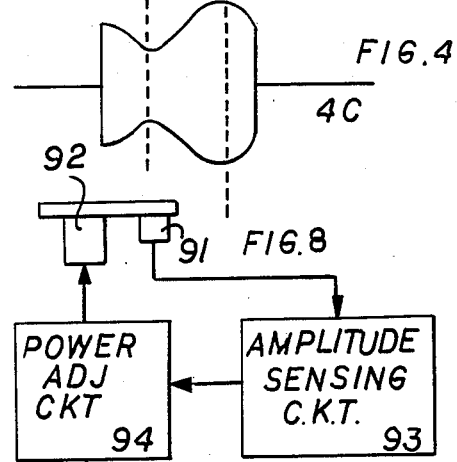
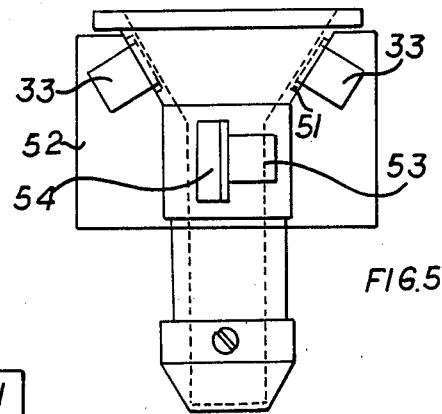
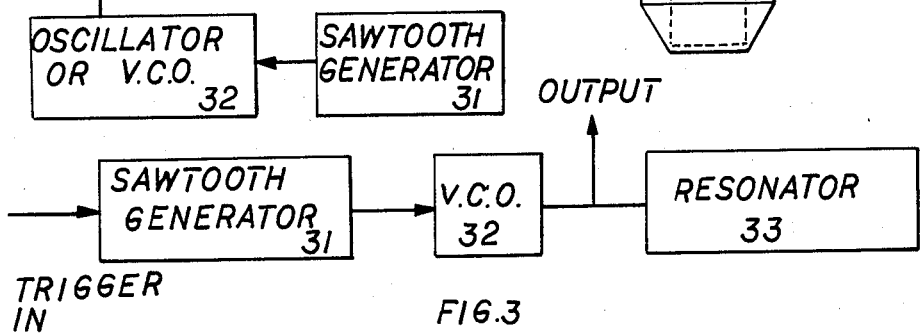

ACOUSTICAL DRY PRODUCT DENSITY SENSOR

FIELD OF THE INVENTION

The present invention relates to density measuring sensors and, more particularly, to devices which measure the density of a dry product such as salt, flour or cement.

BACKGROUND OF THE INVENTION

By government mandate, most dry products must be sold by weight rather than volume. Most granular and powdered products vary in density to such an extent that dispensing equipment, which is usually of the rotating auger type, must be constantly monitored in order to assure that no package has less weight than that specified on the label.

Elaborate means, such as downstream check-weighers, have been devised to remove underweight packages from the conveyor system. In some filling systems, the check-weighers provide feedback to the dispensing equipment, such as an adjustment to the rotational travel of the auger. Such a method lacks accuracy, since the check-weigher is downstream and density of the product may be varying rapidly. In any case, adjustment is made only after an error has been detected.

Another method places the container on a weight scale as it is being filled. The scale automatically stops the auger when the proper weight is attained. Although some error arises as the product continues to fall from the auger as the proper weight is reached, accuracy over the check-weigher feedback system is substantially improved. However, not only is the filling process lengthened considerably, frequent calibration of the weight scale and adjustment of the filling equipment is necessary. Such weight-measurement systems are also impractical for certain types of containers such as envelopes, which must be held in position during filling.

A later development has been the incorporation of microprocessors into some filling systems. The microprocessors make the adjustments necessary for minimizing weight errors on the basis of inputs received from check-weighers, scales, and other sensors which measures the brake and clutch slipage of the auger. Although this technology has improved filling accuracy, the best overall accuracy one can hope to achieve in actual production under ideal conditions (e.g. using a product which exhibits small variations in density) is plus or minus two percent. This means that the packager must adjust the filling machine so that, on the average, it overfills by at least two percent.

Since the auger filling machine dispenses a precise volume for each degree of rotational movement, it is obvious that if the density (weight per unit volume) of the product can be accurately measured, the rotational travel of the auger can be controlled so as to dispense the desired weight.

SUMMARY OF THE INVENTION

It is the object of the present invention to provide a density measuring sensor which provides a high degree of accuracy over a relatively wide range of density variation and measures the product before it is dispensed, thereby eliminating any error due to container variation.

A second object of the invention is to provide a sensor which needs little or no monitoring once the desired weight has been selected.

A third object of this invention is to provide a sensor which automatically checks and corrects itself for degradation due to temperature, humidity and aging.

According to the present invention, a dry product density sensor for measuring the density of granular or powder product is provided. The sensor is contained within a housing which may be installed on an auger filling machine. The sensor comprises one or more resonators such as piezoelectric crystals which preferably resonate in the ultrasonic frequency range. The resonators are positioned so that their sensitive surfaces, directly or through matching material, contact the measured material. The sensor measures acoustic characteristic impedance $(Z_a)$ and the velocity $(C)$ at which sound travels through the material. From these two measurements the density $(P)$ of the material may be derived from the formula $P = Z_a/C$.

Some granular and powdered materials exhibit little or no change in velocity as the sensity varies. This may be attributed to the gas (air) which surrounds the particles and determines the mean velocity. Therefore, in most applications, the velocity measurement can be ignored and the impedance measuring sensor may be calibrated to measure density directly, greatly simplifying the sensor and the electronic circuit design. Many types of ultrasonic transducers are commercially available. The present invention utilizes convenient peizoelectric materials such as barium titanate, lead titanate zirconate or sodium bismuth titanate for the resonators.

BRIEF DESCRIPTION OF THE DRAWINGS

FIG. 1A is a simple resonator circuit;

FIG. 1B is the equivalent circuit for a simple resonator circuit at the resonant frequency;

FIG. 1C is the equivalent circuit for a simple resonator circuit at the anti-resonant frequency;

FIG. 2A is a typical graph of impedance for a resonator with low-density loading;

FIG. 2B is a typical graph of impedance for a resonator with high-density loading;

FIG. 3 is a block diagram showing how the impedance measurement is made;

FIG. 4A is a typical sawtooth ramp voltage signal;

FIG. 4B is a typical graph of voltage vs. frequency for a low-density loading of the resonator;

FIG. 4C is a typical graph of voltage vs. frequency for a high-density loading of the resonator;

FIG. 5 is a simplified elevational view of the density-sensing device mounted at the base of the filler cone on a typical auger-type filling machine;

FIG. 8 is a block diagram showing a secondary embodiment of the invention; coupled with a block diagram showing how output from a driven resonator is amplified and fed back to the driving resonator in order to maintain the vibration level constant.

DESCRIPTION OF THE PREFERRED EMBODIMENTS OF THE INVENTION

Figures 6, 7:
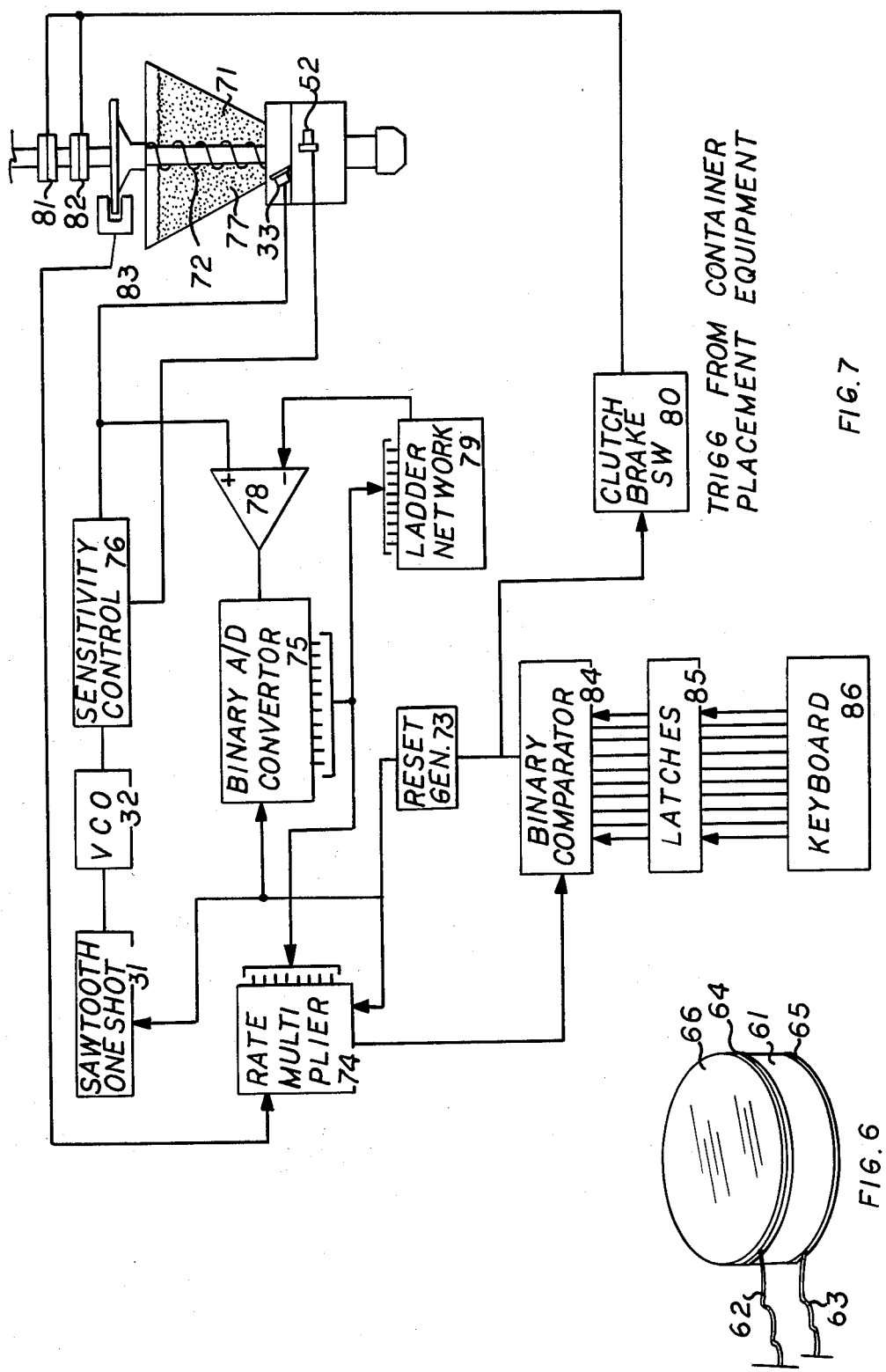
FIG. 6 is a perspective view of a typical lead-titanate-zirconate piezoelectric crystal.
FIG. 7 is a block diagram showing how the sensing device is used to control an auger-type filling machine.

In FIG. 1A, L, C, R and $C_o$ represent the components of the equivalent circuit for a simple acoustic resonator. R represents both internal losses and radiation load; $C_o$ represents the electrical capacitance of the resonator element. When an AC signal is applied to such an L-C-R branch at a frequency where $wL = 1/wC$ (a condition where inductive reactance $X_L$ and capacitive reactance $X_C$ are equal), the effective circuit, shown in FIG. 1B, is said to be purely resistive, at the resonant frequency where impedance is at a minimum. At a slightly higher frequency, the series branch becomes inductive when the inductive component of reactance $X_L$ equals the reactive component of $C_o$; the effective circuit, shown in FIG. 1C, is then at the anti-resonance frequency where impedance is at a maximum. Either the resonant frequency of the anti-resonant frequency or both frequencies may be used to measure the loading effect or density of the dry product. A typical impedance plot for a low-density material is shown in FIG. 2A. An increase in the density of the material will increase $Z_r$ at the resonant frequency and decrease $Z_a$ at the anti-resonant frequency. This effect is illustrated in FIG. 2B.

FIG. 3 is a block diagram which explains the basic density measuring concept. A ramp voltage signal (see FIG. 4A) from sawtooth generator 31 is fed to a voltage controlled oscillator ("VCO") 32. This oscillating signal of increasing frequency is fed to a measuring resonator 33. The initial and final voltage values of the sawtooth ramp are selected so that the output of the VCO is swept through a small frequency range which begins at a frequency equal to or slightly less than the resonant frequency ($f_r$) of measuring resonator 33 and ends at a frequency equal to or slightly greater than the anti-resonant frequency ($f_a$). If the voltage across resonator 33 is measured for a low density loading, an oscillating voltage envelope similar to the graph of FIG. 4B is the result. Measurement with a high density loading results in a graph similar to that shown in FIG. 4C. The density of the load (the dry product) may be determined by measuring both the minimum and maximum output levels or only one level.

As shown in FIG. 5, for applications where product density may vary considerably within the filler cone chamber, two or more measuring resonators 33 may be mounted at in appropriate locations near the base of filler cone 51 within sensor housing 52. The outputs of both measuring resonators 33 are averaged to provide more accurate density measurements.

FIG. 5 also illustrates the use of a reference resonator 53 within the measuring chamber. This resonator is identical to the measuring resonator or resonators except that its sensing surface is pre-loaded with a known density load 54, rather than the measured product load. The output from this resonator is used for calibrating the measuring resonator or resonators in order to compensate for sensitivity changes due to temperature, humidity and aging.

In the preferred embodiment of the invention, the resonator of FIG. 6 is made from a disk-shaped piezoelectric crystal of lead-titanate-zirconate 61 operating in the flexural mode. Input leads 62 and 63 are connected to conductive plates 64 and 65, respectively. The conductive plates are bonded to opposite faces of disk-shaped lead-titanate-zirconate crystal 61. A thin aluminum protector and impedance-matching disk 66 is bonded to the face of the crystal which is to be placed in contact with the material to be measured. The disk services primarily to protect the crystal from abrasion. The type and geometry of crystal may be modified depending on the location of the resonator, the type of material being measured and the general acoustical characteristics of the auger funnel. In some cases, an oblong or tubular crystal operating in the longitudinal mode, or a toroidal one encircling the base of the funnel might be indicated; by completely surrounding the product with such a resonator, average total density may be measured. With proper care in the construction of the resonator so as to minimize parasitic capacitance between the plates of the crystal, a quality factor of greater than one hundred may be obtained. Sensitivity and resolution of one to two percent of full-scale density can be achieved according to the invention with a resonator achieving a quality factor of one hundred and operating about a resonant frequency of 40 KHz. The required frequency sweep range to reach the anti-resonant frequency would be approximately one KHz.

The block diagram of FIG. 7 provides a simple means of explaining how the filling machine is controlled. Measuring resonator 33 is mounted as close as possible to the discharge of the filler cone 71 without incurring interference from the auger 72. When power is applied, reset generator 73 provides one pulse which resets rate multiplier 74, analog-to-digital ("A/D") converter 75 and triggers sawtooth generator 31. Sawtooth generator 31 provides a single sawtooth ramp to VCO 32. The output from VCO 32, which is swept through the resonant and anti-resonant frequencies of measuring resonator 33, is attenuated by sensitivity control 76. The amount of attenuation is determined by the output from reference resonator 52. The voltage level output from sensitivity control 76 is dependent both on the attenuation factor and the impedance of measuring resonator 33. The impedance is, of course, dependent on the acoustical density of the product 77. The resulting signal is applied to the (+) input of voltage comparator 78. As the A/D converter 75 is at reset and all outputs low, the output of ladder network 79 is also low. Voltage comparator 78 provides one square wave pulse for the positive component of each cycle from the oscillating output of VCO 32. For each pulse, A/D converter 75 advances one bit in binary fashion and the output of the ladder network advances one step in staircase fashion. So long as the measurement signal applied to the (+) terminal of voltage comparator 78 continues to increase with each cycle, the voltage reference generated by ladder network 79 tracks the measurement signal. This process continues until the peak output of measuring resonator 33 is at an anti-resonant maximum. With the next cycle, the output of ladder network 79 catches up with the maximum voltage of the signal fed to measuring resonator 33. After the peak has been reached and the voltage begins to drop, the input to the (+) terminal of voltage comparator 78 suddenly becomes less than the input to the (−) terminal. At this point, the pulse output of comparator 78 ceases. The output of A/D converter 75, which corresponds to the maximum excursion of the measurement signal, is applied to rate multiplier 74.

A signal from the container placement equipment turns clutch/brake switch 80 on, which engages clutch 81 and disengages the brake 82, causing auger 72 to rotate. When auger 72 rotates, encoder 83 sends pulses to rate multiplier 74, which outputs pulses to binary comparator 84 at a rate which is a multiple of the encoder pulse rate. The rate multiplier factor is determined by the input received from A/D converter 75. The values for binary comparator 84 are set by means of latches 85 which are preprogrammed by keyboard 86 according to the desired weight of the product. Binary comparator 84 counts the pulses from rate multiplier 74 until they equal the preprogrammed number, at which time it provides a shut-off signal to clutch-brake switch 80, which, by disengaging the clutch and engaging the brake, stops auger 72. The off signal from binary comparator 84 also causes the reset generator 73 to reset the rate multiplier 74, A/D converter 75 and initiates the sawtooth generator 31 to begin another measuring cycle. It is noteworthy that if auger 72 continues to move, after the off signal from the binary comparator 84 due to brake delay or brake wear, rate multiplier 74 having been reset receives pulses from the encoder 83, representing the overtravel of auger 72, and stores them for the next cycle, compensating for the brake delay and wear. Although the first cycle may be overweight, each succeeding cycle would be compensated for.

In a second embodiment of the invention illustrated in FIG. 8, a sensor device is provided which houses one or more pairs of measuring resonators positioned so that the surface of one measuring resonator 91 and each pair of measuring resonators directly, or through impedance matching material, contacts the measured product. A first measuring resonator 91 is mechanically coupled to a second measuring resonator 92. A voltage is induced in second measuring resonator 92 which is proportional to the magnitude of the vibration emitted by the first measuring resonator 91. The induced voltage is measured by amplitude sensing circuit 93, which provides a feedback signal to power adjustment circuit 94. Power adjustment circuit 94 adjusts the amplitude of the oscillating signal produced by VCO 32 and sawtooth generator 31, which is fed to first measuring resonator 91, so that a constant magnitude of ultrasonic vibration from first measuring resonator 91 is maintained. As the density of the product varies, the necessary power applied to the first resonator will change accordingly. The change is measured and used in a circuit similar to that used in the first embodiment so that the filling machine may be controlled to accurately maintain the weight set for the dispensed product. The driving source for the first resonator is designed so as to seek and maintain its output of the resonant or anti-resonant frequency of the resonator. The second resonator 92 should be reasonably broad banded (low Q), or have a resonant frequency other than that of the first resonator, so that a small change in frequency of the first measuring resonator 91 does not change the sensitivity of the second measuring resonator 92. This second embodiment of the invention utilizes a pair of reference resonators, identical to the measuring pair of FIG. 8, except that the first driving resonator is preloaded with material of known density, is provided in order to compensate for changes due to aging and the environment.

While the preferred embodiments of the invention have been disclosed, other embodiments may be devised and modifications made within the spirit of the invention and within the scope of the appended claims.

What is claimed is:

1. In combination with an auger-type product dispensing machine, a device for adjusting the volume of product dispensed as a function of the density of product near the bottom of the filler cone of said dispensing machine in order to dispense an accurate amount of weight of said product comprising:
   (A) at least one measuring pair of acoustical resonators, one resonator of each pair being a driving resonator, the other being a driven resonator, said pair being positioned near the bottom of said filler cone so that the sensing surface of said driving resonator is in acoustical contact with said product, said driven resonator being mechanically coupled to said driving resonator so that a vibration produced by said driven resonator will induce a signal voltage in said driven resonator, said signal voltage being used in a feedback loop to vary the voltage fed to said driven rsonator in order to maintain the magnitude of vibration produced by said driven resonator essentially constant; and
   (B) means for equating changes in the voltage level required to maintain a constant magnitude of ultrasonic vibration output from said driven resonator with changes in the density of said product.

2. The device of claim 1 which further comprises a reference pair of resonators identical to said at least one measuring pair, except that the driving resonator of said reference pair is preloaded with a material of known density, the voltage level induced in said driven reference resonator being compared with the voltage level required to maintain constant the constant magnitude vibration produced by said driven measuring resonator.

3. In combination with an auger-type product dispensing machine, a device for adjusting the volume of product dispensed as a function of the density of product near the bottom of the filler cone of said dispensing machine in order to dispense an accurate amount by weight of said product comprising:
   a reasuring acoustical resonator positioned near the bottom of said filler cone and having its sensing surface in acoustical contact with said product; and
   means for equating changes in the acoustical impedance of said resonator with changes in the density of said product, said equating means comprises:
     means for applying an oscillating force having a variable frequency sweeping through the antiresonant characteristic frequencies of said resonator;
     means for detecting the maximum acoustical impedance of the resonator as the frequency of said oscillating force reaches the antiresonant characteristic frequency of said resonator; and
     means responsive to said means for detecting, for controlling the angular rotation of said auger, said responsive means for controlling comprises means for stopping the movement of said auger as a function of its rotational travel multiplied by the detected maximum acoustical impedance.

4. The device of claim 3 wherein said means for stopping comprises:
   (A) an optical encoder coupled to the auger drive shaft, said optical encoder generating a discrete pulse for each given increment of said auger's angular movement;
   (B) a rate multiplier designed to multiply the cumulative value of said discrete pulses by a value proportional to said maximum acoustical impedance; and
   (C) a comparator for monitoring the output of the rate multiplier and for generating an auger stopping signal when said output reached a predetermined limit.

5. The device of claim 3 wherein said means for stopping comprises:
   (A) an optical encoder coupled to the auger drive shaft, said optical encoder generating a discrete pulse for each given increment of said auger's angular movement;

(B) a rate multiplier designed to multiply the cumulative value of said discrete pulses by a value proportional to said maximum acoustical impedance; and (C) a comparator for monitoring the output of the rate multiplier and or generating an auger stopping signal when said output reaches a predetermined limit.

6. In combination with an auger-type product dispensing machine, a device for adjusting the volume of product dispensed as a function of the density of product near the bottom of the filler cone of said dispensing machine in order to dispense an accurate amount by weight of said product comprising:

a measuring acoustical resonator positioned near the bottom of said filler cone and having its sensing surface in acoustical contact with said product; and means for equating changes in the acoustical impedance of said resonator with changes in the density of said product, said equating means comprises:

means for applying an oscillating force having a variable frequency sweeping through the antiresonant charactertistic frequencies of said resonator;

means for detecting the maximum acoustical impedance of the resonator as the frequency of said oscillating force reaches the antiresonant characteristic frequency of said resonator, said means for detecting comprises an analog-to-digital converter;

means for advancing said analog-to-digital converter one bit for each cycle of said oscillating force;

a ladder network for converting the output of said analog-to-digital converter into a tracking voltage; and an analog signal comparator, said comparator receiving said tracking voltage at its reference terminal and a signal proportional to said acoustical impedance at its input terminal; and said comparator further controlling the input of said analog-to-digital converter; and means, responsive to said means for detecting, for controlling the angular rotation of said auger.

7. In combination with an auger-type product dispensing machine, a device for adjusting the volume of product dispensed as a function of the density of product near the bottom of the filler cone of said dispensing machine in order to dispense an accurate amount by weight of said product comprising:

(A) a measuring acoustical resonator positioned near the bottom of said filler cone and having its sensing surface in acoustical contact with said product; and (B) means for equating changes in the acoustical impedance of said resonator with changes in the density of said product, said equating means comprises:

a. means for applying an oscillating force having a variable frequency sweeping through the resonant characteristic frequencies of said resonator;

b. means for detecting the minimum acoustical impedance of the resonator as the frequency of said oscillating force reaches the resonant characteristic frequency of said resonator; and c. means responsive to said means for detecting, for controlling the angular rotation of said auger, said means for controlling comprises means for stopping the movement of said auger as a function of its rotations rotational travel multiplied by the detected maximum acoustical impedance.

8. In combination with an auger-type product dispensing machine, a device for adjusting the volume of product dispensed as a function of the density of product near the bottom of the filler cone of said dispensing machine in order to dispense an accurate amount by weight of said product comprising:

a measuring acoustical resonator positioned near the bottom of said filler cone and having its sensing surface in acoustical contact with said product; and means for equating changes in the acoustical impedance of said resonator with changes in the density of said product, said equating means comprises:

a. means for applying an oscillating force having a variable frequency sweeping through the antiresonant characteristic frequencies of said resonator;

b. means for detecting the minimum acoustical impedance of the resonator as the frequency of said oscillating force reaches the resonant characteristic frequency of said resonator, said detecting means comprises:

an analog-to-digital converter;

means for advancing said analog-to-digital converter one bit for each cycle of said oscillating force;

ladder network for converting the output of said analog-to-digital converter into a tracking voltage; and an analog signal comparator; said comparator receiving said tracking voltage at its reference terminal and a signal proportional to said acoustical impedance at its input terminal; and said comparator further controlling the input to said analog-to-digital converter; and means, responsive to said means for detecting, for controlling the angular rotation of said auger.

* * * * *